United States Patent [19]
Weiss et al.

[11] Patent Number: 5,984,951
[45] Date of Patent: *Nov. 16, 1999

[54] ICE COOLING MEDICAL DEVICE AND METHOD

[76] Inventors: Craig R. Weiss, 49 Biltmore Estates, Phoenix, Ariz. 85017; Robert Hu, 1625 E. Westwind, Phoenix, Ariz. 85283

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/838,181

[22] Filed: Apr. 16, 1997

Related U.S. Application Data

[63] Continuation of application No. 07/891,215, May 29, 1992, which is a continuation of application No. 07/678,010, Apr. 11, 1991, Pat. No. 5,117,823.

[51] Int. Cl.$^6$ ........................................................ A61F 7/10
[52] U.S. Cl. ........................................... 607/109; 607/112
[58] Field of Search ........................... 607/108–112, 144; 383/901; 62/530

[56] References Cited

U.S. PATENT DOCUMENTS

| | | | |
|---|---|---|---|
| 783,827 | 2/1905 | Gasaway et al. | 128/403 |
| 1,169,123 | 1/1916 | Burns | 128/402 |
| 1,739,625 | 12/1929 | Wolters | 128/402 |
| 4,951,666 | 8/1990 | Inman et al. | 128/402 |
| 5,016,629 | 5/1991 | Kanare | 607/114 |
| 5,074,300 | 12/1991 | Murphy | 128/402 |
| 5,117,823 | 6/1992 | Weiss et al. | 607/109 |

*Primary Examiner*—Mark S. Graham
*Attorney, Agent, or Firm*—Harry M. Weiss; Jeffrey Weiss; Paul W. Davis

[57] ABSTRACT

An ice cooling apparatus and method therefor that comprise a number of ice pockets slideably attached to an adjustable strap for securing them in place around a wearer's body. By positioning the ice pockets on the painful areas, a wearer is assured of continuous contact and cooling effect, with the attendant benefits resulting from ice treatment. Because the apparatus is strapped around the wearer's body, it is not necessary to use one's hands to keep it in place, thus allowing the wearer to be freed from the usual constraint of having to hold the ice bag on the sore site.

14 Claims, 1 Drawing Sheet

ICE COOLING MEDICAL DEVICE AND METHOD

RELATED APPLICATION

This application is a Continuation U.S. patent application Ser. No. 07/891,215; filed May 29, 1992 which a continuation of application Ser. No. 07/678,010, filed Apr. 1, 1991 which is now U.S. Pat. No. 5,117,823; issued Jun. 2, 1992.

BACKGROUND OF THE INVENTION

1. Field of the Invention

This invention pertains to the general field of medical devices and methods for cooling body parts to alleviate pain and inflammation. In particular, it provides a new medical device and a new method especially useful for the application of ice to the cheeks of a patient after oral surgery or other dental procedure.

2. Description of the Prior Art

It is common for dentists and oral surgeons to recommend the application of ice to the sore cheeks of a patient to reduce pain after oral surgery or other major procedure. Typically, a patient will hold an ice pack on the sore spot with one hand or will try to balance it in place while lying down. In either case, the person's ability to function normally is impaired by a certain loss of mobility. Therefore, it would be very useful and desirable to have a cooling device that could be worn around a person's cheeks, thus freeing him or her from the aforementioned constraints.

Several types of garments have been developed in the past to provide a cooling effect to the body of people working in hot environments. For example, mine rescuers often perform their duty in areas near fires and must wear heavily insulated protective gear. The addition of cooling garments to their normal clothing helps alleviate heat stress problems during mine rescue operations.

The cooling function of these devices is produced by the presence of cool water or ice in well placed reservoirs distributed throughout the garment. In some models, cold water is circulated through the garment in a system of flexible tubes; in others, dry ice is used to maximize the cooling capacity of the garment. In U.S. Pat. No. 4,033,354 (1977), De Rosa discloses an ice cooling vest consisting of sealed pockets containing water and removably attached to the garment around the body of a wearer. These water-filled pockets are frozen and affixed to the inside of the vest to provide the desired cooling and are later separated to be frozen again for future use.

It does not appear that anyone has developed a cooling apparatus for dental patients in the form of a wearable garment. Therefore, a need still exists for a practical device that provides the necessary cooling effect on a continuous basis and that can be worn without impairing the wearer's ability to function normally.

BRIEF SUMMARY OF THE INVENTION

It is therefore an objective of this invention to provide an ice cooling apparatus that can be strapped around a person's head and that does not require the use of the person's hands to continuously keep it in place to apply ice to a painful area.

Another objective of the invention is that it be suitable for use by anyone, regardless of head size and facial characteristics.

Another goal of the invention is that the cooling apparatus be adaptable for use on other parts of the body, such as strapped around an arm or a leg.

A further goal of the invention is that it be reusable, either by charging it with new ice or by refreezing water-filled permanent pockets.

Still another objective of this invention is the realization of the above mentioned goals in an economical and commercially viable manner. This is done by utilizing simple components and methods of manufacture that are either already available in the open market or can be developed at competitive prices.

In accordance with these and other objectives, the ice cooling apparatus of this invention comprises a number of ice pockets slideably attached to an adjustable strap for securing them in place around a wearer's face or other part of the body. By positioning the ice pockets on the painful areas, a wearer is assured of continuous contact and cooling effect, with the attendant benefits resulting from ice treatment. Because the apparatus is strapped around the wearer's body part, it is not necessary to use one's hands to keep it in place, thus allowing the wearer to be freed from the usual constraint of having to hold the ice bag on the sore site.

Various other purposes and advantages of the invention will become clear from its description in the specifications that follow, and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose only one of the various ways in which the invention may be practiced.

DETAILED DESCRIPTION OF THE INVENTION

Figure 1:
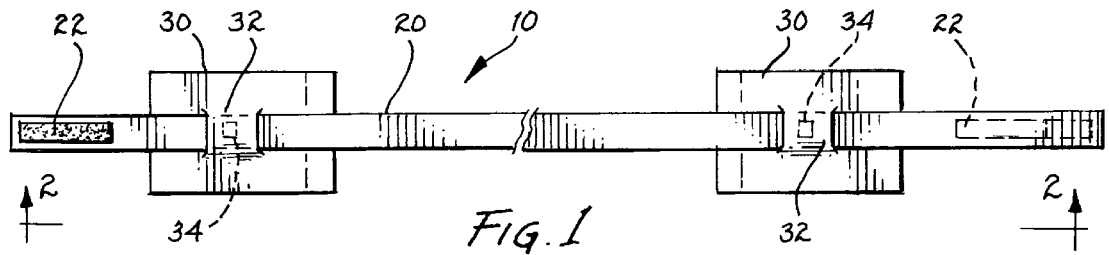
FIG. 1 is a plan view of one embodiment of the ice cooling apparatus of this invention, showing two ice pockets attached to a strap with fastening means at each end.
Figure 2:
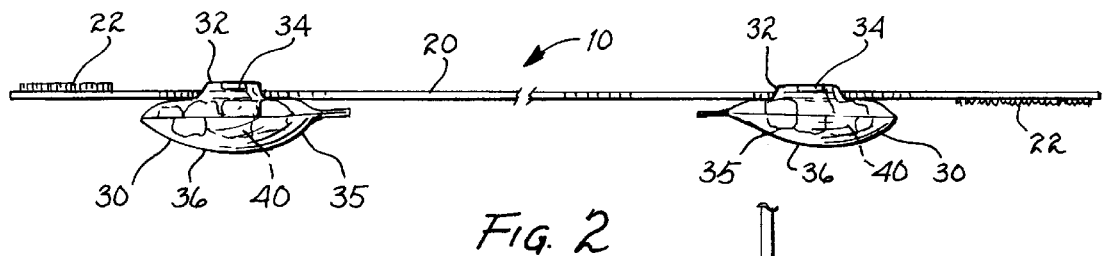
FIG. 2 is a view of the same embodiment of the invention taken from line 2—2 in FIG. 1.

The heart of this invention lies in the novel approach adopted to apply ice to a patient after oral surgery or other injuries requiring a similar procedure. Since the condition of the patient may not permit him or her alone to effectively keep the ice on the pain area for the required period of time, the apparatus of this invention can be worn to produce the desired result without anyone's help. In addition, the wearer's hands are kept free and he or she can, therefore, be active without unnecessary constraints.

Referring to the drawings, wherein the same numerals and symbols are used throughout to designate like parts, a plan view of one embodiment of the invention is shown in FIG.

Figure 4:
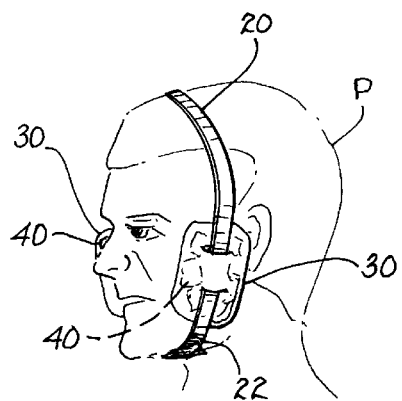
FIG. 4 shows a perspective view of a patient wearing the ice cooling apparatus of the invention to provide cooling around his cheeks.

1. The ice cooling apparatus 10 comprises a strap 20 of sufficient length to wrap around a wearer's head, as illustrated in FIG. 4. Fastening means 22, preferably of the fiber loop type, normally sold under the trademark "Velcro," are affixed to each end of the strap for easy interconnection to form a tight continuous loop. Ice pockets 30 for the retention of ice or other cold media are slideably attached to the strap 20 by way of loops 32 in the ice pocket through which the strap is threaded. A strip of double-sided adhesive tape 34, or other equivalent device, is provided between the inside surface of each loop 32 and the strap 20 in order to retain each pocket in place after it has been slid to the desired position for the proper point of contact after placement on the user's head or other body part.

Figure 3:
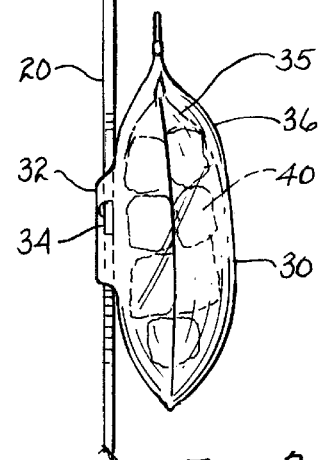
FIG. 3 is a perspective view of one method of construction of the ice pockets of this invention, such that their position can be adjusted to contact the sore sites on the wearer's body.

As shown in detail in the preferred embodiment of FIG. 3, each ice pocket 30 consists of a first, outer, plastic bag 36 containing a second, inner, plastic bag 35. Both bags can be closed to form a sealed enclosure by means of the type known by the trademark "Ziploc" or by any other, equivalent, closure. The strap loops 32 are formed by cutting two parallel incisions in one side of the outer bag 36, so that the strap 20 can be inserted therethrough in the same manner that a belt is passed through belt loops. Before application to a wearer's cheeks (or other body part) for treatment, the inner bag 35 is filled with ice pieces 40, or with any other cooling medium, such as dry ice. Alternatively, the ice bag 35 could itself be a water-filled sealed ice bag to be frozen before use. Although the embodiment shown in the figures features two ice pockets, it is understood that such number could be increased or decreased to fit the need of the user simply by inserting more or less ice pockets through the strap 20.

Figure 5:
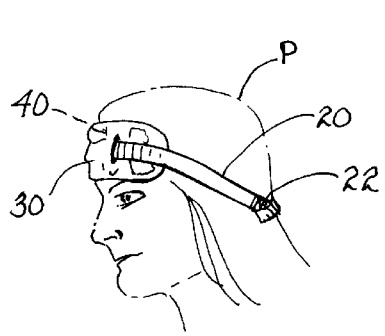
FIG. 5 shows a perspective view of a patient wearing the ice cooling apparatus of the invention to provide cooling on her forehead.
Figure 6:
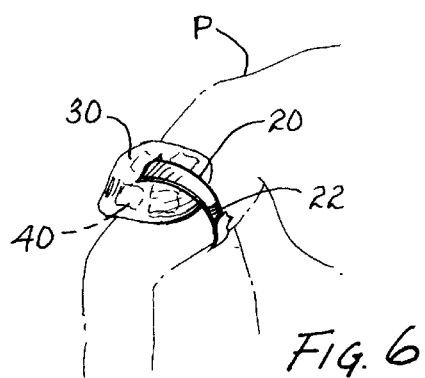
FIG. 6 shows a perspective view of a patient wearing the ice cooling apparatus of the invention to provide cooling around an arm.

In use, the ice cooling apparatus 10 of this invention can be applied to the face of a person P by wrapping it around the head with the ice pockets 30 against the cheeks on the inside of the strap 20, as illustrated in FIG. 4. If the direct contact of the ice pockets with the wearer's face produces too much cold for comfort, the apparatus 10 can be worn with the ice pocket on the outside of the strap, so that the cold medium will be less directly in contact with the person's skin and, therefore, more comfortable for long periods of wear. FIG. 5 and 6 illustrate the use of the ice cooling apparatus in similar applications on a wearer's forehead and arm.

While the described preferred embodiment consists of disposable plastic bags and a "Velcro$^R$"—fitted strap, it is understood that many equivalent designs are possible within the scope of the invention. The most important characteristics include the adjustability of the position of the ice pockets, their waterproofness, and the overall lightness of the apparatus. Those skilled in the art could easily design other embodiments of the invention with alternative components, such as sealed ice bags removably attached to a strap through a continuous strip of fiber loop fastener fitted along the length of the strap.

Thus, various changes in the details, steps and materials that have been described may be made by those skilled in the art within the principles and scope of the invention herein illustrated and defined in the appended claims. While the present invention has been shown and described herein in what is believed to be the most practical and preferred embodiment, it is recognized that departures can be made therefrom within the scope of the invention, which is therefore not to be limited to the details disclosed herein, but is to be accorded the full scope of the claims so as to embrace any and all equivalent apparatus and methods.

We claim:

1. An apparatus for alleviating pain in areas of the body of a wearer through cold treatment comprising, in combination a single strap;

means coupled to said single strap comprising an inner independently moveable and removable plastic bag having a cold medium located therein for containing the cold medium in a waterproof condition, said plastic bags having means for permitting rapid opening and closing of a portion thereof; and means removably and slideably connected to said single strap for completely enclosing said inner plastic bag comprising a larger entirely thin walled plastic bag and for slidable movement along said single strap including both removal, from and addition to said single strap of said larger thin walled plastic bag containing said inner plastic bag containing the cold medium, said single strap penetrating said larger thin walled plastic bag into the interior of said larger thin walled plastic bag to permit removable connection to said larger thin walled plastic bag, adjustment of said larger thin walled plastic bag along the single strap and strapping said larger thin walled plastic bag around a portion of the wearer's body in contact with an area requiring cold treatment.

2. The apparatus of claim 1 wherein inner bag has a rib and groove sealing portion.

3. The apparatus of claim 2 wherein both said inner plastic bag and said larger bag have a rib and groove sealing portion.

4. The apparatus of claim 1 wherein said larger plastic bag having apertures located in a surface portion of said larger plastic bag, said single strap penetrating said apertures of said larger plastic bag, said larger plastic bag slideably coupled to said single strap for movement therealong as said single strap is moved through said apertures of said larger plastic bag.

5. The apparatus of claim 4 wherein said apertures consisting of two spaced apart slits in said surface portion of said larger plastic bag.

6. The apparatus of claim 1 including a plurality of larger plastic bags coupled to said single strap each of said plurality of larger plastic bags containing an inner independently movable and removable plastic bag having the cold medium therein and means for permitting rapid opening and closing of a portion thereof.

7. The apparatus of claim 6 wherein each of said plurality of larger plastic bags is slideably coupled for movement along said single strap.

8. A method of alleviating pain in areas of a person's body by cold treatment comprising the steps of:

providing a single strap;

providing means coupled to said single strap comprising an inner independently moveable and removable plastic bag having a cold medium located therein for containing the cold medium in a waterproof condition, said plastic bag having means for permitting rapid opening and closing of a portion thereof; and providing means removably and slideably connected to said single strap for completely enclosing said inner plastic bag with a larger entirely thin walled plastic bag and for slidable movement along said single strap including both removal from and addition to said single strap of said larger thin walled plastic bag containing said inner plastic bag containing the cold medium, said single strap penetrating said larger thin walled plastic bag into the interior of said larger thin walled plastic bag to permit removable connection to said larger thin walled plastic bag, adjustment of said larger thin walled plastic bag along the single strap and strapping said larger thin walled plastic bag around a portion of the person's body in contact with an area requiring cold treatment.

9. The method of claim 8 wherein said inner bag having a rib and groove sealing portion.

10. The method of claim 5 wherein both said inner plastic bag and said larger bag have a rib and groove sealing portion.

11. The method of claim 4 wherein said larger plastic bag having apertures located in a surface portion of said larger plastic bag, said single strap penetrating said apertures of said larger plastic bag, said larger plastic bag slideably coupled to said single strap for movement therealong as said single strap is moved through said apertures of said larger plastic bag.

12. The method of claim 11 wherein said apertures consisting of two spaced apart slits in said surface portion of said larger plastic bag.

13. The method of claim 4 including a plurality of larger plastic bags coupled to said single strap each of said plurality of larger plastic bags containing an inner independently movable and removable plastic bag having the cold medium therein and means for permitting rapid opening and closing of a portion thereof.

14. The method of claim 13 wherein each of said plurality of larger plastic bags is slideably coupled for movement along said single strap.

* * * * *